United States Patent
Jin et al.

(10) Patent No.: US 9,938,228 B2
(45) Date of Patent: Apr. 10, 2018

(54) PROCESS FOR THE PREPARATION OF SPIRO[2.5]OCTANE-5,7-DIONE AND SPIRO[3.5]NONANE-6,8-DIONE

(71) Applicant: Boehringer Ingelheim International GmbH, Ingelheim am Rhein (DE)

(72) Inventors: Xiangle Jin, Shanghai (CN); Weitong Dong, Shanghai (CN); Yan Fu, Shanghai (CN); Jun Lu, Shanghai (CN); Le Xie, Shanghai (CN); Wei Xu, Shanghai (CN); Jinsong Yang, Shanghai (CN); Qian Zhu, Shanghai (CN)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/509,504

(22) PCT Filed: Aug. 28, 2015

(86) PCT No.: PCT/CN2015/088345
§ 371 (c)(1),
(2) Date: Mar. 8, 2017

(87) PCT Pub. No.: WO2016/037534
PCT Pub. Date: Mar. 17, 2016

(65) Prior Publication Data
US 2017/0247315 A1    Aug. 31, 2017

(30) Foreign Application Priority Data
Sep. 9, 2014 (WO) ............... PCT/CN2014/086143

(51) Int. Cl.
| | | |
|---|---|---|
| C07C 69/74 | (2006.01) |
| C07C 69/608 | (2006.01) |
| C07C 69/757 | (2006.01) |
| C07C 69/716 | (2006.01) |
| C07C 67/347 | (2006.01) |
| C07C 59/205 | (2006.01) |
| C07C 45/67 | (2006.01) |
| C07C 45/54 | (2006.01) |

(52) U.S. Cl.
CPC ............ *C07C 69/608* (2013.01); *C07C 45/54* (2013.01); *C07C 45/673* (2013.01); *C07C 59/205* (2013.01); *C07C 67/347* (2013.01); *C07C 69/716* (2013.01); *C07C 69/757* (2013.01)

(58) Field of Classification Search
None
See application file for complete search history.

(56) References Cited

U.S. PATENT DOCUMENTS

2005/0043341 A1   2/2005  Gielen
2008/0194609 A1   8/2008  Bischoff et al.

FOREIGN PATENT DOCUMENTS

| WO | 2012052451 | 4/2012 |
| WO | 2012085166 | 6/2012 |
| WO | 2014020038 | 2/2014 |

OTHER PUBLICATIONS

Lehmann, Organic Process Research and Development, Process Development and Pilot Plant Scale Synthesis of Spiro[3.5]nonane-6,8-dione, 2003 p. 913-916.
International Search Report, for PCT/CN2015/088345, PCT/ISA220, dated Jan. 12, 2016.

*Primary Examiner* — Clinton A Brooks
*Assistant Examiner* — Ana Z Muresan
(74) *Attorney, Agent, or Firm* — Marc Began; David L. Kershner

(57) ABSTRACT

This invention relates to methods for the synthesis of spiro[2.5]octane-5,7-dione and spiro[3.5]nonane-6,8-dione which are useful as intermediates in the manufacture of pharmaceutically active ingredients.

1 Claim, No Drawings

PROCESS FOR THE PREPARATION OF SPIRO[2.5]OCTANE-5,7-DIONE AND SPIRO[3.5]NONANE-6,8-DIONE

RELATED APPLICATIONS

The application claims the priority to PCT Application PCT/CN2014/086143, filed on Sep. 9, 2014.

TECHNICAL FIELD

This invention relates to methods for the synthesis of spiro[2.5]octane-5,7-dione and spiro[3.5]nonane-6,8-dione which are useful as intermediates in the manufacture of pharmaceutically active ingredients.

BACKGROUND

The compounds spiro[2.5]octane-5,7-dione and spiro[3.5]nonane-6,8-dione are useful and important intermediates for the preparation of pharmaceutically active substances. Several routes to them are known and are quite challenging. However, they all suffer from severe drawbacks from a chemical process point of view. Therefore, it is a demand for developing efficient and robust methods to synthesize spiro[2.5]octane-5,7-dione and spiro[3.5]nonane-6,8-dione in order to circumvent these problems.

Up to now, several routes to synthesize spiro[2.5]octane-5,7-dione and spiro[3.5]nonane-6,8-dione have been described in published papers or patents applications.

WO 2012052451 and WO 2012085166 describe a four-step (two operations) synthesis of spiro[2.5]octane-5,7-dione (3) via Wittig reaction, Michael/Claisen reactions followed by hydrolysis and decarboxylation using (1-ethoxycyclopropoxy)trimethylsilane (1) as the starting material (Scheme 1). The disadvantage of this approach is that flash chromatography is used for the purification of intermediate and final product, which is not practical for scale-up. Additionally, the use of o-dichlorobenzene and sodium hydride which is used quite often on laboratory scale is not ideal in the pilot or manufacture scale either.

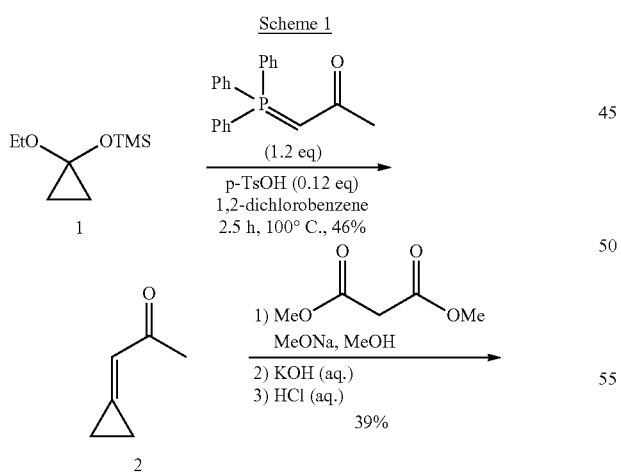

Angew. Chem. Intl. Ed., 38(22), 3373-3375, 1999 describes the synthesis of spiro[3.5]nonane-6,8-dione (6) via a similar protocol as above. The starting material is cyclobutanone (4). Due to the less activity of the Wittig reagent (MeC(O)CH=PPh$_3$) and the low volatile property of cyclobutanone (4), the first step can only be carried out at 100° C. to increase the reactivity and in silicon oil to avoid the loss of cyclobutanone (4) from the reaction system. After the reaction, the enone (5) has to be distilled out from the silicon oil in order to proceed to the next step (Scheme 2).

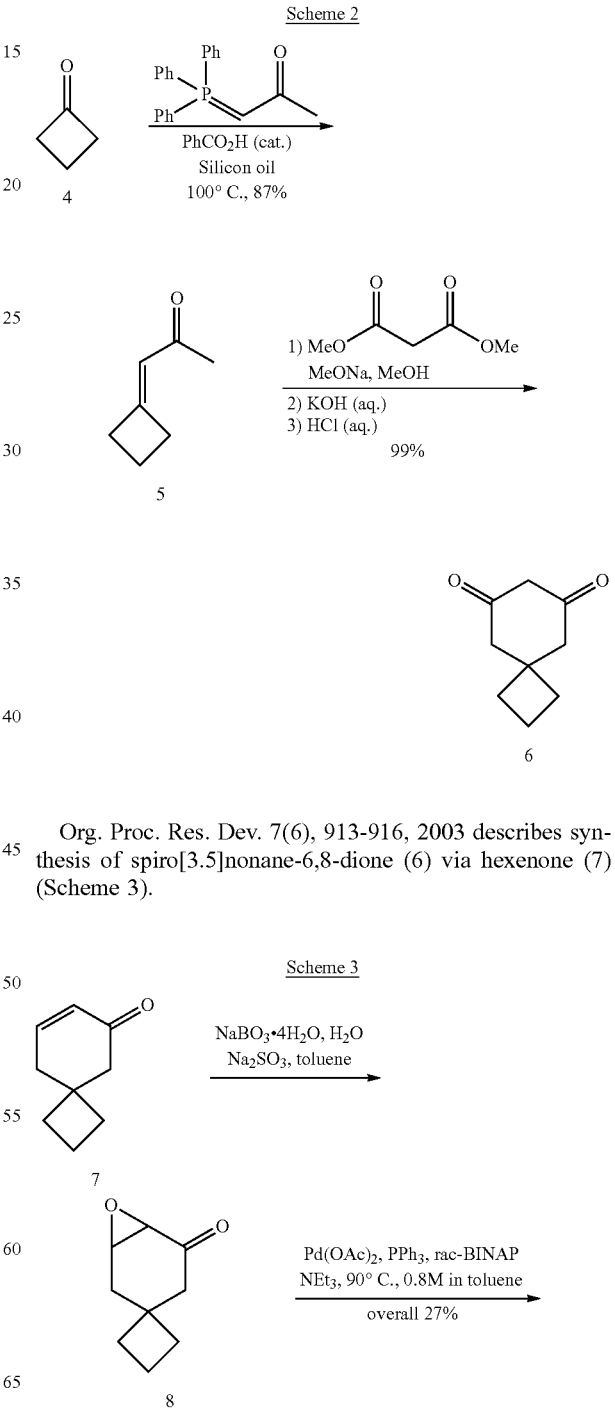

Org. Proc. Res. Dev. 7(6), 913-916, 2003 describes synthesis of spiro[3.5]nonane-6,8-dione (6) via hexenone (7) (Scheme 3).

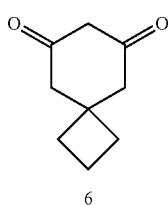

Therefore, there is a strong need for developing a novel and practical process to synthesize spiro[2.5]octane-5,7-dione (3) and/or spiro[3.5]nonane-6,8-dione (6), which could allow to use the above mentioned starting materials ((1-ethoxycyclopropoxy)trimethylsilane (1) and/or cyclobutanone (4)) and provide the desired products in high quality and good chemical yield without involvement of chromatography purification and usage of uncommon organic solvents and reagents.

DESCRIPTION OF THE INVENTION

The present invention provides two independent efficient processes for the synthesis of spiro[2.5]octane-5,7-dione (via Process A or Process B) and/or spiro[3.5]nonane-6,8-dione (via Process A) as described herein below.

A general process for preparing spiro[2.5]octane-5,7-dione is outlined in Scheme 4. In one embodiment, the present invention is directed to the general multi-step synthetic method for preparing spiro[2.5]octane-5,7-dione as set forth in Scheme 4 below. In other embodiments, the invention is directed to each of the individual steps of Scheme 4 and any combination of two or more successive steps of Scheme 4. The invention may also be directed to the intermediate compounds, e.g. as set forth in Scheme 4.

Scheme 4: Process A for the manufacture of spiro[2.5]octane-5,7-dione according to the invention (aspect 1 of the invention):

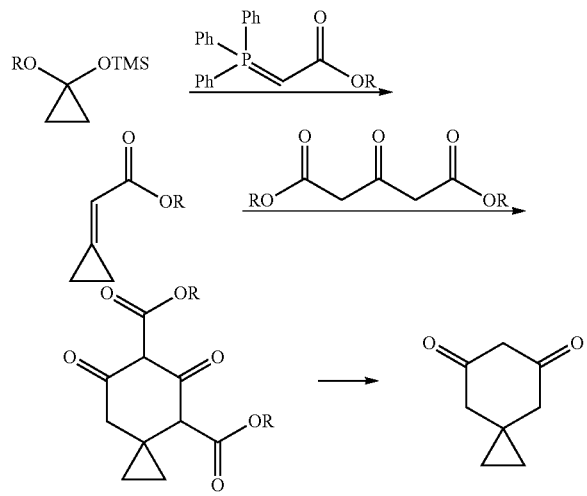

In Scheme 4, the substituent R may be independently selected from alkyl, such as e.g. independently selected from C1-C6 alkyl, preferably C1-C4 alkyl (such as e.g. methyl, ethyl, propyl, isopropyl, or the like), more preferably C1-C3 alkyl or even more preferably C1-C2 alkyl, particularly ethyl.

Accordingly, in Scheme 4 the group C(O)OR represents an ester group, preferably an alkyl ester group, where R may be independently selected from alkyl, such as e.g. independently selected from C1-C6 alkyl, preferably C1-C4 alkyl (such as e.g. methyl, ethyl, propyl, isopropyl, or the like), more preferably C1-C3 alkyl or even more preferably C1-C2 alkyl, particularly ethyl.

Thus, in one aspect, the present invention relates to a process for the manufacture of spiro[2.5]octane-5,7-dione having the formula

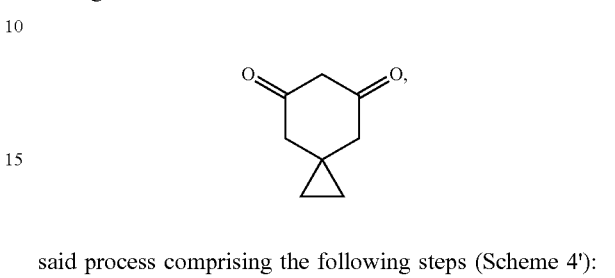

said process comprising the following steps (Scheme 4'):

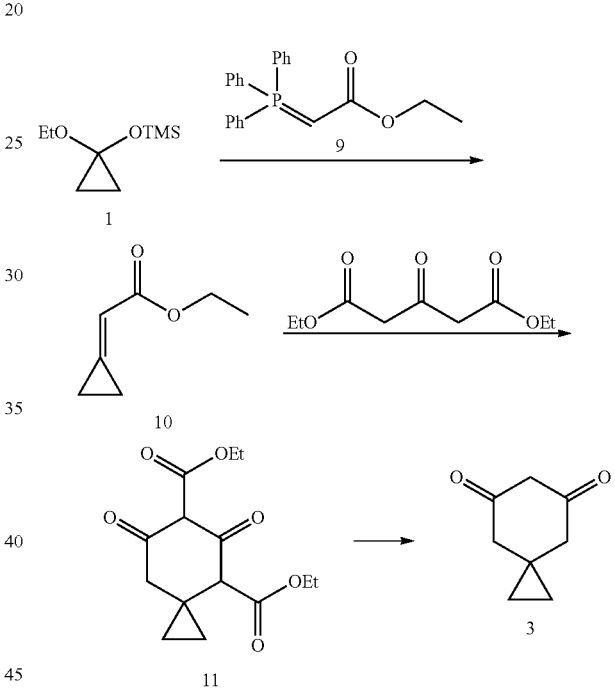

For example, certain embodimental details may be one or more of the following (Scheme 4"):

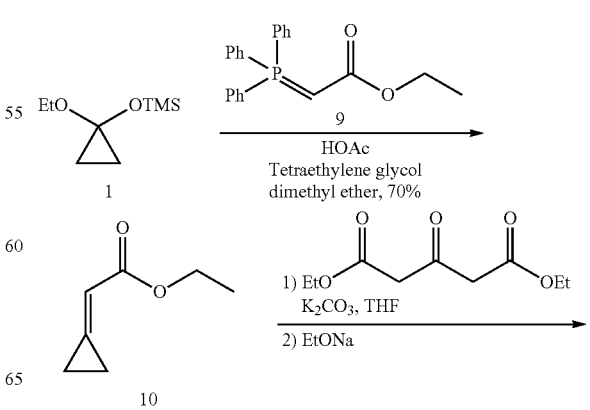

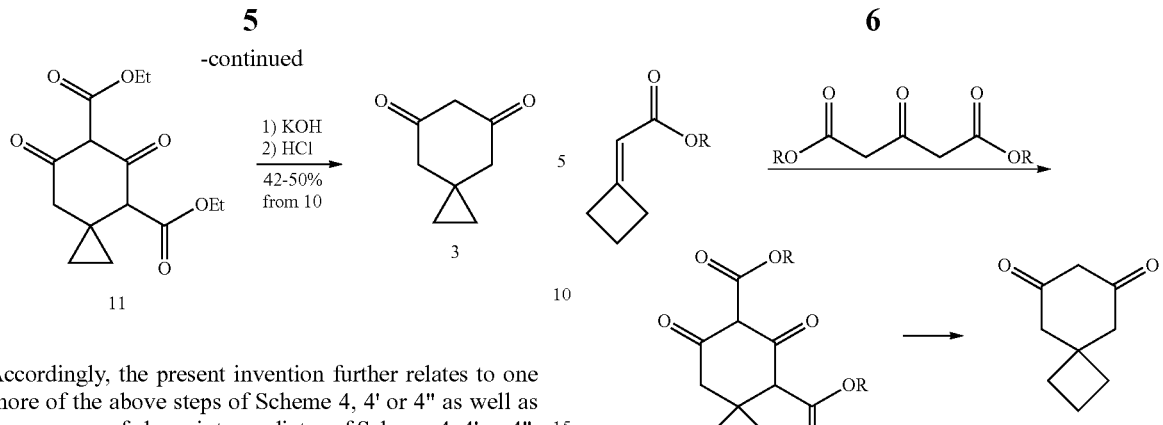

Accordingly, the present invention further relates to one or more of the above steps of Scheme 4, 4' or 4" as well as to one or more of above intermediates of Scheme 4, 4' or 4".

With reference to the steps shown in Scheme 4, 4' and 4" of the invention, a process or method according to the present invention comprises one or more of the following:

reacting a (1-alkoxycyclopropoxy)trimethylsilane [e.g. (1-ethoxycyclopropoxy)trimethylsilane (1)] with a Wittig reagent (9) to form a cyclopropylidene carboxylic acid alkyl ester [e.g. cyclopropylidene carboxylic acid ethyl ester (10)] (such as e.g. in the presence of a suitable acid, such as acetic acid, in a suitable solvent, such as high boiling point solvent (e.g. tetraethylene glycol dimethyl ether). Preferably, a high boiling point solvent (such as tetraethylene glycol dimethyl ether) is used in this step in order to purify the low boiling point product by distillation and make it more practical in a plant), cyclizing cyclopropylidene carboxylic acid alkyl ester [e.g. cyclopropylidene carboxylic acid ethyl ester (10)] with dialkyl 1,3-acetonedicarboxylate [e.g. diethyl 1,3-acetonedicarboxylate] to form 5,7-dioxo-spiro[2.5]octane-4,6-dicarboxylic acid dialkyl ester [e.g. 5,7-dioxo-spiro[2.5]octane-4,6-dicarboxylic acid diethyl ester (11), which may be isolated or not] (such as e.g. in the presence of a suitable organic or inorganic base (e.g. $K_2CO_3$ followed by EtONa) in a suitable solvent, such as $K_2CO_3$ in THF, followed by addition of EtONa in EtOH), saponification (ester hydrolysis) of (isolated or non-isolated) 5,7-dioxo-spiro[2.5]octane-4,6-dicarboxylic acid dialkyl ester [e.g. 5,7-dioxo-spiro[2.5]octane-4,6-dicarboxylic acid diethyl ester (11)] with the aid of a suitable base (such as alkali hydroxide, e.g. aqueous KOH) and decarboxylation (e.g. under acidic conditions, such as by heating with HCl) to form spiro[2.5]octane-5,7-dione (3), optionally, crystallization or recrystallization of crude spiro[2.5]octane-5,7-dione (3) such as from MTBE (methyl tert-butyl ether) to obtain purified spiro[2.5]octane-5,7-dione (3).

The yield is 42%-50% (from intermediate 10) and the purity is >98% purity without any chromatography.

A general process for preparing spiro[3.5]nonane-6,8-dione is outlined in Scheme 5. In one embodiment, the present invention is directed to the general multi-step synthetic method for preparing spiro[3.5]nonane-6,8-dione as set forth in Scheme 5 below. In other embodiments, the invention is directed to each of the individual steps of Scheme 5 and any combination of two or more successive steps of Scheme 5. The invention may also be directed to the intermediate compounds, e.g. as set forth in Scheme 5.

Scheme 5: Process for the manufacture of spiro[3.5]nonane-6,8-dione according to the invention (aspect 2 of the invention):

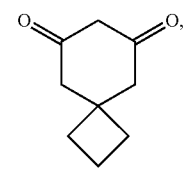

In Scheme 5, the substituent R may be independently selected from alkyl, such as e.g. independently selected from C1-C6 alkyl, preferably C1-C4 alkyl (such as e.g. methyl, ethyl, propyl, isopropyl, or the like), more preferably C1-C3 alkyl or even more preferably C1-C2 alkyl, particularly ethyl.

Accordingly, in Scheme 5 the group C(O)OR represents an ester group, preferably an alkyl ester group, where R may be independently selected from alkyl, such as e.g. independently selected from C1-C6 alkyl, preferably C1-C4 alkyl (such as e.g. methyl, ethyl, propyl, isopropyl, or the like), more preferably C1-C3 alkyl or even more preferably C1-C2 alkyl, particularly ethyl.

Thus, in another aspect, the present invention relates to a process for the manufacture of spiro[3.5]nonane-6,8-dione having the formula

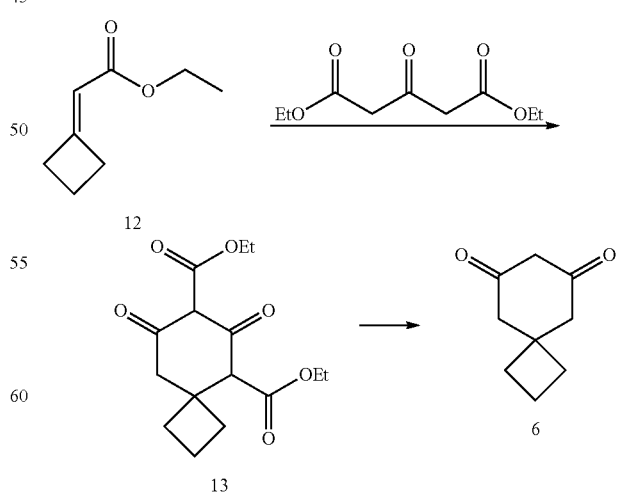

said process comprising the following steps (Scheme 5'):

For example, certain embodimental details may be one or more of the following (Scheme 5"):

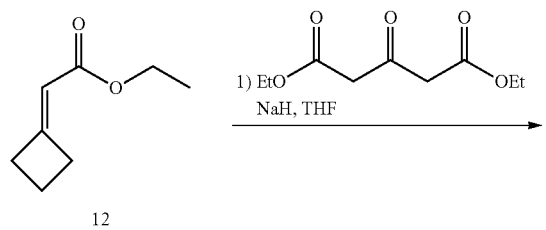

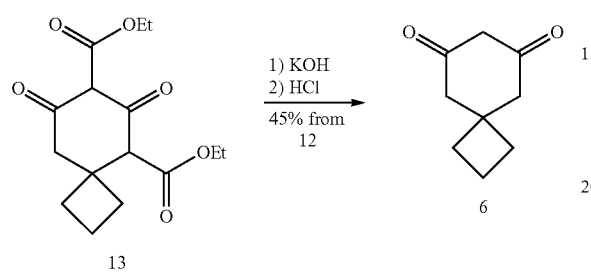

Accordingly, the present invention further relates to one or more of the above steps of Scheme 5, 5' or 5" as well as to one or more of above intermediates of Scheme 5, 5' or 5".

With reference to the steps shown in Scheme 5, 5' and 5" of the invention, a process or method according to the present invention comprises one or more of the following:

- cyclizing cyclobutylidene carboxylic acid alkyl ester [e.g. cyclobutylidene carboxylic acid ethyl ester (12), cf. WO 2004/054564] with dialkyl 1,3-acetonedicarboxylate [e.g. diethyl 1,3-acetonedicarboxylate] to form 6,8-dioxo-spiro[3.5]nonane-5,7-dicarboxylic acid dialkyl ester [e.g. 6,8-dioxo-spiro[3.5]nonane-5,7-dicarboxylic acid diethyl ester (13), which may be isolated or not] (such as e.g. in the presence of a suitable organic or inorganic base (e.g. NaH followed by EtONa) in a suitable solvent, such as NaH in THF, followed by addition of EtONa in EtOH),
- saponification (ester hydrolysis) of (isolated or non-isolated) 6,8-dioxo-spiro[3.5]nonane-5,7-dicarboxylic acid dialkyl ester [e.g. 6,8-dioxo-spiro[3.5]nonane-5,7-dicarboxylic acid diethyl ester (13)] with the aid of a suitable base (such as alkali hydroxide, e.g. aqueous KOH) and decarboxylation (e.g. under acidic conditions, such as by heating with HCl) to form spiro[3.5]nonane-6,8-dione (6),
- optionally, crystallization or recrystallization of crude spiro[3.5]nonane-6,8-dione (3) such as from MTBE (methyl tert-butyl ether) to obtain purified spiro[3.5]nonane-6,8-dione (6).

The overall yield is about 45% from intermediate (12).

Alternatively, a general process for preparing spiro[2.5]octane-5,7-dione is outlined in Scheme 6. In one embodiment, the present invention is directed to the general multi-step synthetic method for preparing spiro[2.5]octane-5,7-dione as set forth in Scheme 6 below. In other embodiments, the invention is directed to each of the individual steps of Scheme 6 and any combination of two or more successive steps of Scheme 6. The invention may also be directed to the intermediate compounds, e.g. as set forth in Scheme 6.

Scheme 6: Process B for the manufacture of spiro[2.5]octane-5,7-dione according to the invention (aspect 3 of the invention):

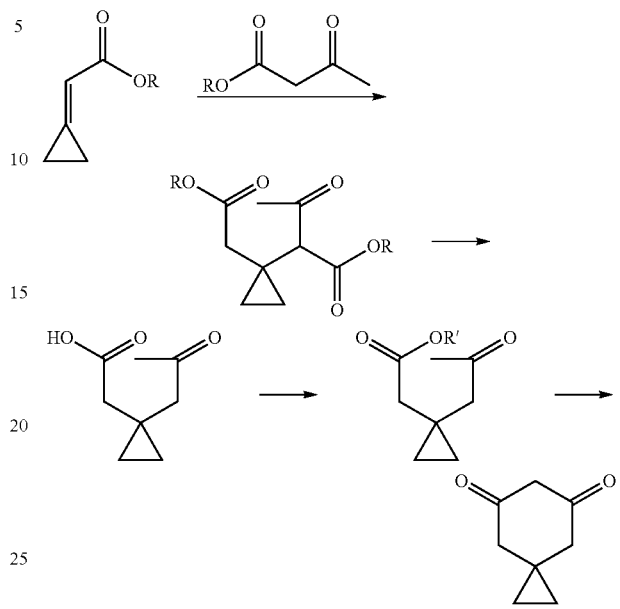

In Scheme 6, the substituents R and R' may be independently selected from alkyl, such as e.g. independently selected from C1-C6 alkyl, preferably C1-C4 alkyl (such as e.g. methyl, ethyl, propyl, isopropyl, or the like), more preferably C1-C3 alkyl or even more preferably C1-C2 alkyl, particularly R is ethyl and/or R' is methyl.

Accordingly, in Scheme 6 the groups C(O)OR and C(O)OR' represent an ester group, respectively, preferably an alkyl ester group, where R and R' may be independently selected from alkyl, such as e.g. independently selected from C1-C6 alkyl, preferably C1-C4 alkyl (such as e.g. methyl, ethyl, propyl, isopropyl, or the like), more preferably C1-C3 alkyl or even more preferably C1-C2 alkyl, particularly R is ethyl and/or R' is methyl.

Thus, in another aspect, the present invention relates to a process for the manufacture of spiro[2.5]octane-5,7-dione having the formula

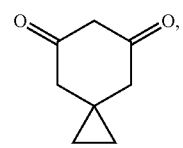

said process comprising the following steps (Scheme 6'):

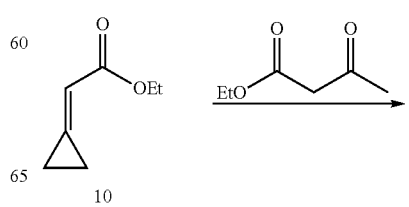

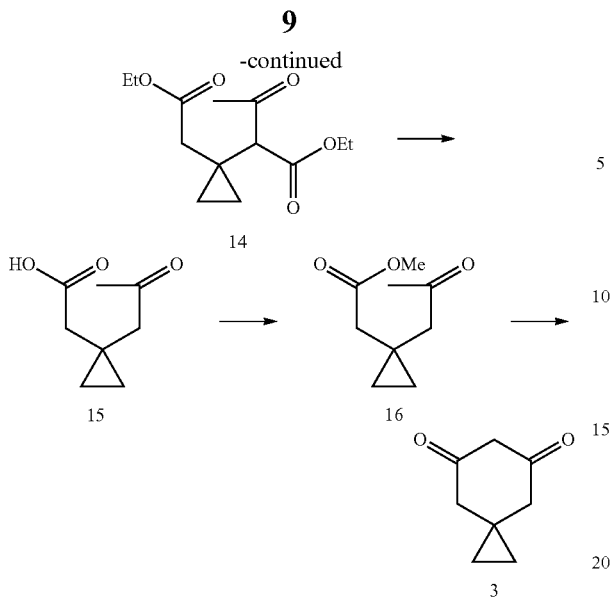

For example, certain embodimental details may be one or more of the following (Scheme 6"):

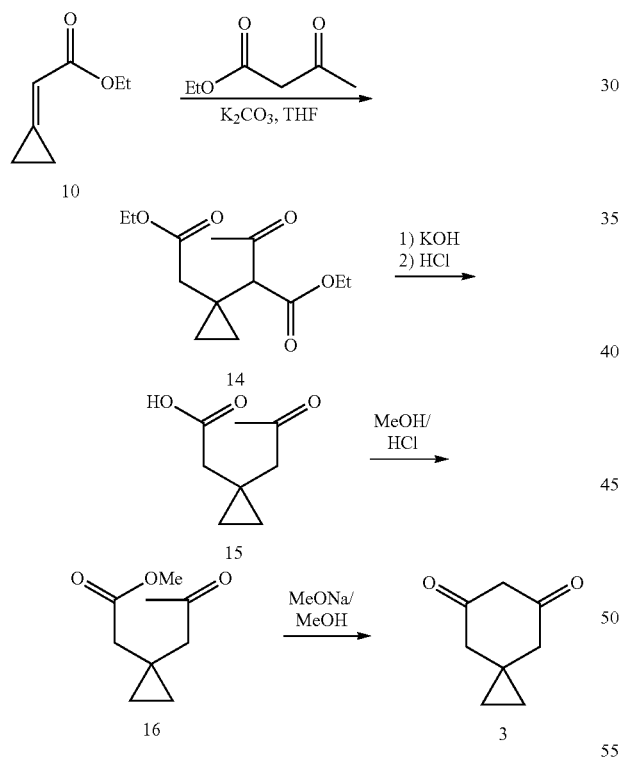

Accordingly, the present invention further relates to one or more of the above steps of Scheme 6, 6' or 6" as well as to one or more of above intermediates of Scheme 6, 6' or 6".

With reference to the steps shown in Scheme 6, 6' and 6" of the invention, a process or method according to the present invention comprises one or more of the following:

reacting cyclopropylidene carboxylic acid alkyl ester [e.g. cyclopropylidene carboxylic acid ethyl ester (10)] with alkyl acetoacetate [e.g. ethyl acetoacetate] to form 2-(1-alkoxycarbonylmethyl-cyclopropyl)-3-oxo-butyric acid alkyl ester [e.g. 2-(1-ethoxycarbonylmethyl-cyclopropyl)-3-oxo-butyric acid ethyl ester (14)], which may be isolated or not] (such as e.g. in the presence of a suitable organic or inorganic base (e.g. $K_2CO_3$) in a suitable solvent, such as $K_2CO_3$ in THF), saponification (ester hydrolysis) of (isolated or non-isolated) 2-(1-alkoxycarbonylmethyl-cyclopropyl)-3-oxo-butyric acid alkyl ester [e.g. 2-(1-ethoxycarbonyl-methyl-cyclopropyl)-3-oxo-butyric acid ethyl ester (14)] with the aid of a suitable base (such as alkali hydroxide, e.g. aqueous NaOH) and decarboxylation (e.g. under acidic conditions, such as by heating with HCl) to form [1-(2-oxo-propyl)cyclopropyl]acetic acid (15), esterification of [1-(2-oxo-propyl)cyclopropyl]acetic acid (15) to form [1-(2-oxo-propyl)cyclopropyl]acetic acid alkyl ester [e.g. [1-(2-oxo-propyl)cyclopropyl]acetic acid methyl ester (16)] (such as in methanol in the presence of HCl), cyclizing [1-(2-oxo-propyl)cyclopropyl]acetic acid alkyl ester [e.g. [1-(2-oxo-propyl)cyclopropyl]acetic acid methyl ester (16)] to form spiro[2.5]octane-5,7-dione (3) (such as e.g. in the presence of a suitable organic or inorganic base (e.g. MeONa in MeOH), optionally, crystallization or recrystallization of crude spiro[2.5]octane-5,7-dione (3) such as from MTBE (methyl tert-butyl ether) to obtain purified spiro[2.5] octane-5,7-dione (3).

Spiro[2.5]octane-5,7-dione (3) is obtained in a 62% yield with 98.6% HPLC purity.

When this protocol is used starting from Compound 12, the major isolated product from this reaction is Compound 18 instead of Compound 17. It is assumed that the Michael Addition intermediate goes through a reminiscent Billys-Hillman type reaction (Scheme 7).

Scheme 7

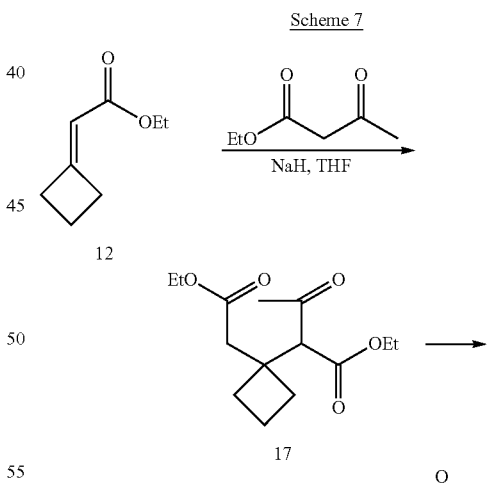

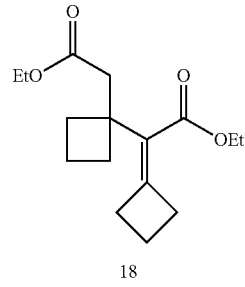

In certain more detailed embodiments of the invention, the present invention relates to the process and/or the individual process steps substantially as described by way of example in the following examples.

Further, the invention relates to a compound useful as intermediate selected from:

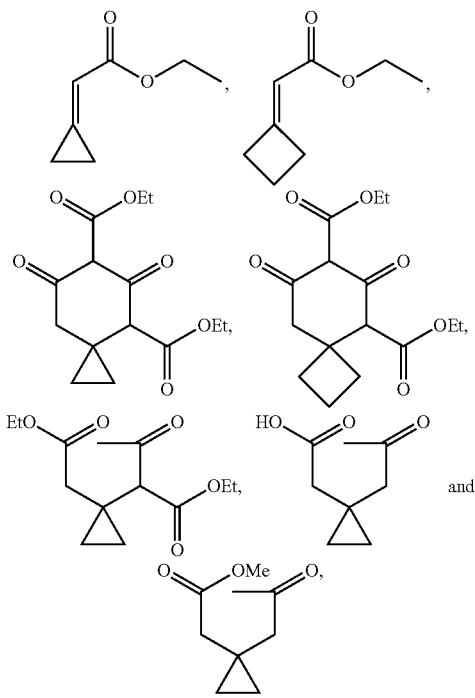

or a tautomer or salt thereof.

Furthermore, the invention relates to a compound useful as intermediate selected from:

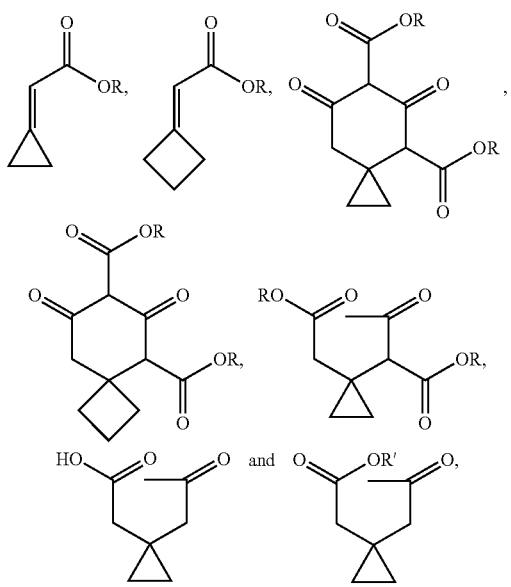

in each of which R and/or R' may be independently hydrogen or C1-C6 alkyl, preferably C1-C4 alkyl (such as e.g. methyl, ethyl, propyl, isopropyl, or the like), more prefer-ably C1-C3 alkyl or even more preferably C1-C2 alkyl, particularly R is ethyl and/or R' is methyl, or a tautomer or salt thereof.

In a further embodiment, the present invention is not limited to the use of a ethyl or methyl ester of formula

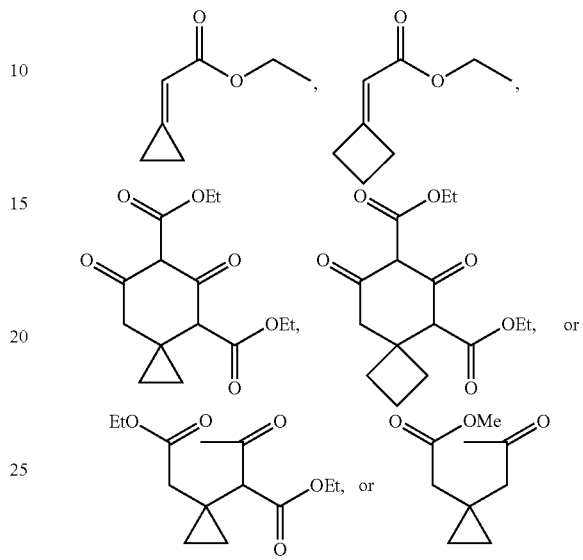

within the processes or methods according to the present invention; in addition to the respective ethyl esters, a broader genus of esters of formula

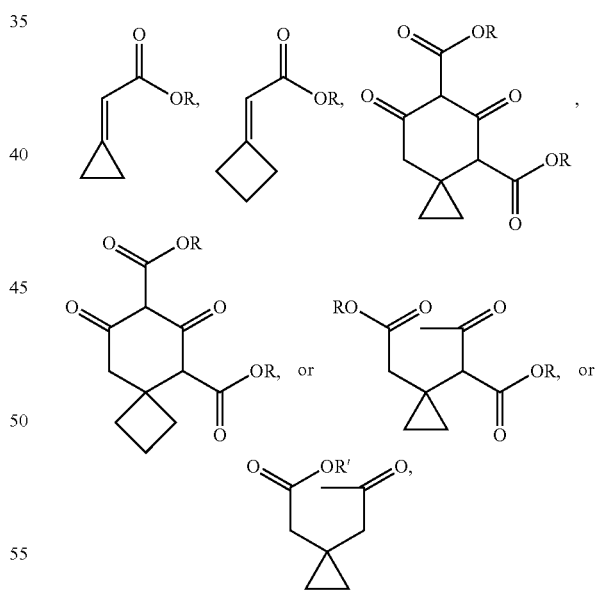

in each of which R and/or R' may be independently C1-C6 alkyl, preferably C1-C4 alkyl (such as e.g. methyl, ethyl, propyl, isopropyl, or the like), more preferably C1-C3 alkyl or even more preferably C1-C2 alkyl, particularly R is ethyl and/or R' is methyl, may be considered.

Accordingly, in alternative embodiments, the present invention refers to processes or methods as disclosed herein above or herein below (e.g. Scheme 1 or Scheme 2) wherein a compound of formula

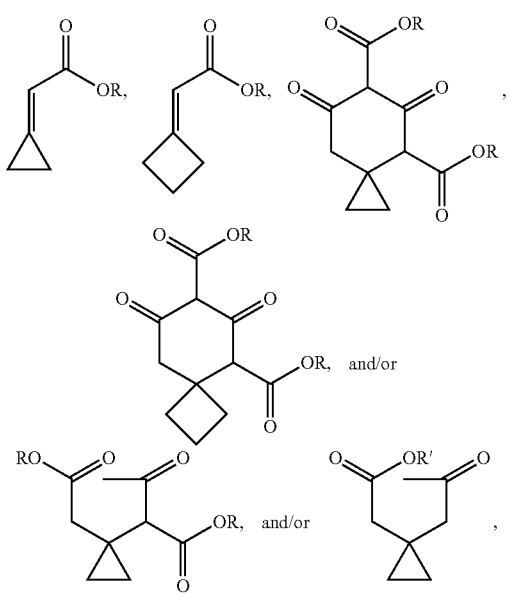

in each of which R and/or R' is independently C1-C6 alkyl, preferably C1-C4 alkyl (such as e.g. methyl, ethyl, propyl, isopropyl, or the like), more preferably C1-C3 alkyl or even more preferably C1-C2 alkyl, particularly R is ethyl and/or R' is methyl, is used or involved instead of a compound of formula

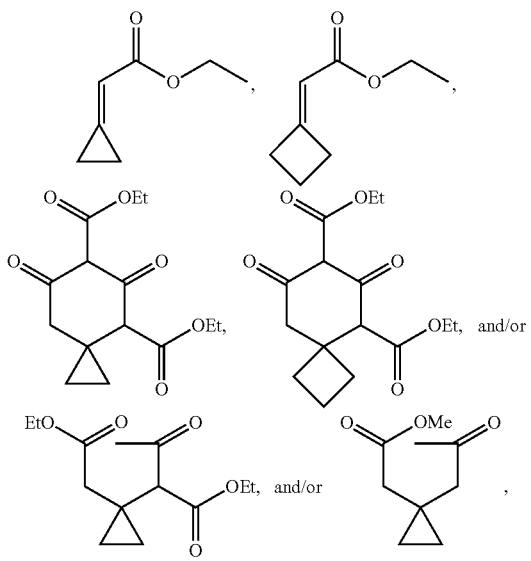

respectively.

In certain embodiments, the present invention relates to an indicated intermediate or final compound in isolated form, such as e.g. in solid, amorphous or crystalline form.

In certain embodiments, the present invention relates to an indicated intermediate in solution form (such as e.g. present in a reaction solvent).

Further, the present invention relates to spiro[2.5]octane-5,7-dione or spiro[3.5]nonane-6,8-dione each obtainable or obtained by a process or method according to the present invention.

In an embodiment, the present invention relates to spiro [2.5]octane-5,7-dione isolated (e.g. crystallized) from MTBE (methyl tert-butyl ether).

In an embodiment, the present invention relates to spiro [3.5]nonane-6,8-dione isolated (e.g. crystallized) from MTBE (methyl tert-butyl ether).

Further, the present invention relates in particular to a process for preparing spiro[2.5]octane-5,7-dione having the formula

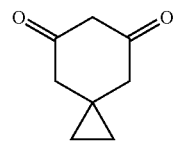

comprising one or more of the following:

cyclization of cyclopropylidene carboxylic acid alkyl ester having the formula

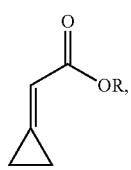

e.g. cyclopropylidene carboxylic acid ethyl ester, with dialkyl 1,3-acetonedicarboxylate having the formula

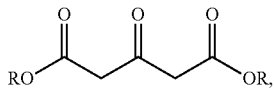

e.g. diethyl 1,3-acetonedicarboxylate, to form 5,7-dioxo-spiro[2.5]octane-4,6-dicarboxylic acid dialkyl ester having the formula

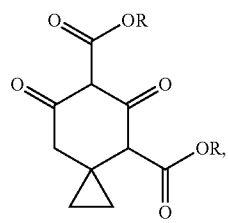

e.g. 5,7-dioxo-spiro[2.5]octane-4,6-dicarboxylic acid diethyl ester, wherein R may be independently C1-C6 alkyl, preferably C1-C4 alkyl (such as e.g. methyl, ethyl, propyl, isopropyl, or the like), more preferably C1-C3 alkyl or even more preferably C1-C2 alkyl, particularly R is ethyl;

ester hydrolysis and decarboxylation of 5,7-dioxo-spiro [2.5]octane-4,6-dicarboxylic acid dialkyl ester having the formula

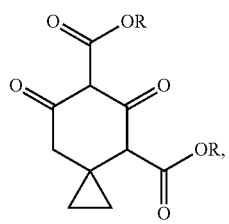

e.g. 5,7-dioxo-spiro[2.5]octane-4,6-dicarboxylic acid diethyl ester, to form spiro[2.5]octane-5,7-dione, wherein R may be independently C1-C6 alkyl, preferably C1-C4 alkyl (such as e.g. methyl, ethyl, propyl, isopropyl, or the like), more preferably C1-C3 alkyl or even more preferably C1-C2 alkyl, particularly R is ethyl.

Further, the present invention relates in particular to a process for preparing spiro[3.5]nonane-6,8-dione having the formula

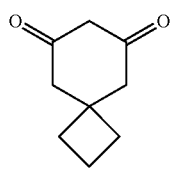 [SMILES: O=C1CC(=O)CC2(CCC2)C1]

comprising one or more of the following:
cyclization of cyclobutylidene carboxylic acid alkyl ester having the formula

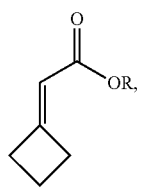

e.g. cyclobutylidene carboxylic acid ethyl ester, with dialkyl 1,3-acetonedicarboxylate having the formula

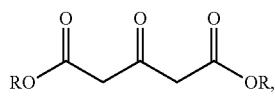

e.g. diethyl 1,3-acetonedicarboxylate, to form 6,8-dioxo-spiro[3.5]nonane-5,7-dicarboxylic acid dialkyl ester having the formula

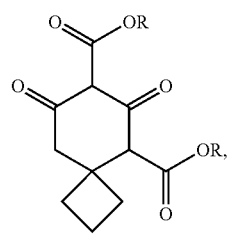

e.g. 6,8-dioxo-spiro[3.5]nonane-5,7-dicarboxylic acid diethyl ester, wherein R may be independently C1-C6 alkyl, preferably C1-C4 alkyl (such as e.g. methyl, ethyl, propyl, isopropyl, or the like), more preferably C1-C3 alkyl or even more preferably C1-C2 alkyl, particularly R is ethyl;

ester hydrolysis and decarboxylation of 6,8-dioxo-spiro[3.5]nonane-5,7-dicarboxylic acid dialkyl ester having the formula

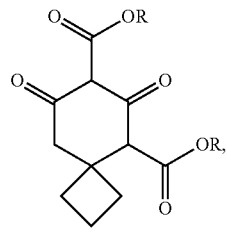

e.g. 6,8-dioxo-spiro[3.5]nonane-5,7-dicarboxylic acid diethyl ester, to form spiro[3.5]nonane-6,8-dione, wherein R may be independently C1-C6 alkyl, preferably C1-C4 alkyl (such as e.g. methyl, ethyl, propyl, isopropyl, or the like), more preferably C1-C3 alkyl or even more preferably C1-C2 alkyl, particularly R is ethyl.

Further, the present invention relates in particular to a process for preparing spiro[2.5]octane-5,7-dione having the formula

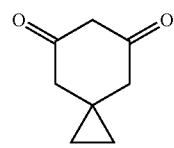

comprising one or more of the following:
cyclization of [1-(2-oxo-propyl)cyclopropyl]acetic acid alkyl ester having the formula

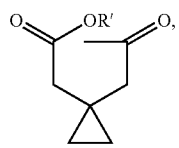

e.g. [1-(2-oxo-propyl)cyclopropyl]acetic acid methyl ester, to form spiro[2.5]octane-5,7-dione,
wherein R' may be independently C1-C6 alkyl, preferably C1-C4 alkyl (such as e.g. methyl, ethyl, propyl, isopropyl, or the like), more preferably C1-C3 alkyl or even more preferably C1-C2 alkyl, particularly R' is methyl.

The intermediates and final compounds of the invention may be obtained using methods of synthesis known in principle, or analogously or similarly to known procedures. Preferably, the intermediates involved and the final compounds may be obtained by the following methods according to the invention which are described in more detailed example herein after.

The process steps may be performed substantially as described herein by way of example. A process or method of this invention may comprise one or more steps of converting and/or reacting the mentioned intermediates with the appropriate reaction partners, suitably under conditions as disclosed herein (e.g. by using the indicated reagents and/or solvents and/or temperatures, etc.).

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by gas chromatography (GC), High Pressure Liquid Chromatography (HPLC) or Thin Layer Chromatography, if desired.

SYNTHETIC EXAMPLES

In order that this invention be more fully understood, the following examples are set forth. These examples are for the purpose of illustrating preferred embodiments of this invention, and are not to be construed as limiting the scope of the invention in any way.

Example 1: Preparation of Cyclopropylidene Carboxylic Acid Ethyl Ester (Compound 10)

To a mixture solution of 100 g of 1-ethoxy-1-(trimethylsiloxy)cyclopropane (1) and 17.1 g AcOH in 400 mL tetraethylene glycol dimethyl ether, was added 180 g (2-ethoxy-2-oxoethylidene)triphenylphosphorane which was dissolved in 270 mL of dichloromethane dropwise at 90-100° C. for 3 h. During the adding period, dichloromethane was removed by distillation to keep the process temperature at 90-100° C. The mixture was stirred at 90-100° C. for another 1 h, which allowed dichloromethane be removed completely by distillation. Then the product (10) was purified by fractional distillation at 10 mbar (cooling temperature of fluid in condenser should not be above −10° C., all distillate was collected as the product). A total 50-55 g (yield: 69-76%) of Compound 10 was obtained as a colorless liquid. $^1$H NMR (400 MHz, DMSO-$d_6$) δ 6.22 (m, 1H), 4.13 (q, 2H, J=7.2 Hz), 1.45-1.38 (m, 2H), 1.30-1.20 (m, 2H), 1.22 (t, 3H, J=7.2 Hz); $^{13}$C NMR (100 MHz, CDCl$_3$) δ 165.7, 144.5, 110.4, 59.6, 20.1, 13.7, 13.5; MS (m/z) [M-28] 98.1.

Example 2: Preparation of Spiro[2.5]octane-5,7-dione (Compound 3)

To a mixture slurry of K$_2$CO$_3$ (43.8 g) in THF (200 mL), were added diethyl acetonedicarboxylate (76.9 g) and compound 10 (40.0 g) dropwise respectively at 20-30° C. The mixture was stirred at 20-30° C. for 1 h. A total of 215.7 g of NaOEt solution (20% in EtOH) was added dropwise at below 40° C. for 30 min. The mixture was refluxed for 3 h. A total of 354.7 g of KOH solution (20% in water) was added slowly to keep the reaction mixture at slight reflux. The reaction mixture was then refluxed for 5 h. The organic solvent in reaction mixture was removed at reduced pressure. The resulting aqueous phase was washed with MTBE (2×100 mL). Then the aqueous phase was heated to 50-60° C., at this temperature conc. HCl was added dropwise until pH was adjusted to 2.5-3.0. It was stirred for another 1 h, and then cooled to 20-30° C. Water (200 mL) was added and the resulting aqueous solution was extracted with MTBE (3×300 mL). The combined organic phase was concentrated under vacuum. Then, another 30 mL of MTBE was added to the residue, and slurry was stirred for 30 min at 0-10° C., the first portion of the product was collected by filtration. The filtrate was concentrated under vacuum again and then 20 mL of MTBE was added. After the slurry was stirred at 0-10° C. for 0.5 h, the second portion of the product was also collected by filtration. The combined product was washed with 5 mL of MTBE, and then dried under vacuum. A total of 19.5 g (44% yield, 99% purity) of Compound 3 was obtained as a white solid. $^1$H NMR (400 MHz, DMSO-$d_6$) δ 11.05 (s, br 1H), 5.25 (s, 1H), 2.15 (s, 4H), 0.35 (s, 4H); $^{13}$C NMR (100 MHz, DMSO-$d_6$) δ 178.61, 103.96, 41.76, 14.95, 10.85; MS (m/z) 138.1.

Example 3: Preparation of Cyclobutylidene Carboxylic Acid Ethyl Ester (Compound 12)

To a slurry of NaH (8.0 g, 60% in oil) in THF (150 mL), was added triethyl phosphonoacetate (44.8 g) in 25 mL of THF dropwise at 0-10° C. over 40 min. The reaction mixture was stirred at 0-10° C. for another 0.5 h. Then cyclobutanone (14.0 g) in 25 mL of THF was added dropwise at 0-10° C. over 30 min. The reaction mixture was stirred at 0-10° C. for 2 h. A total of 50 mL of water was then added slowly at 20-30° C. The organic solvent was removed under reduced pressure followed by addition of 150 mL of water. The aqueous solution was extracted with MTBE (3×100 mL). The combined organic phase was washed with water (100 mL). It was then dried over anhydrous MgSO$_4$. Filtration followed by evaporation gave the crude product, which was purified by fractional distillation at 81-82° C./19 mbar to give 22.2 g (79% yield, 99% purity) of Compound 12 as a colorless liquid. $^1$H NMR (400 MHz, CDCl$_3$) δ 5.56 (m, 1H), 4.13 (q, 2H, J=7.2 Hz), 3.12 (m, 2H), 2.81 (m, 2H), 2.08 (m, 2H), 1.25 (t, 3H, J=7.2 Hz); $^{13}$C NMR (100 MHz, DMSO-$d_6$) δ 167.2, 165.3, 111.8, 58.9, 33.3, 31.8, 17.1, 14.0; MS (m/z) 140.1.

Example 4: Preparation of Spiro[3.5]nonane-6,8-dione (Compound 6)

To a slurry of NaH (0.96 g, 60% in oil) in THF (5.0 mL), was added diethyl acetonedicarboxylate (2.4 g) slowly at 0-15° C. After it was stirred for 0.5 h, a total of 1.4 g of Compound 12 was added slowly at 0-15° C. The mixture was stirred at 20-30° C. for 1 h, and then heated to reflux. 5 mL of EtOH and 2.4 g of NaOEt solution (20% in EtOH) were added respectively. The resulting mixture was refluxed for 5 h. After that, a total of 11.2 g of KOH solution (20% in water) was added slowly, and the reaction mixture was continuously refluxed for another 5 h. The organic solvent in reaction mixture was removed under vacuum. The aqueous solution was extracted with MTBE (2×10 mL) and then heated to 50-60° C. with addition of conc. HCl until pH at 2.5-3.5. The resulting mixture was stirred at 50-60° C. for 2 h and then cooled to 20-30° C. It was extracted with dichloromethane (3×25 mL). The combined organic phase was concentrated under vacuum. Then 5.0 mL of MTBE was added to the residue and the resulting slurry was stirred for 0.5 h at 0-10° C. The solid was collected by filtration, washed with MTBE (5.0 mL), and dried under vacuum. A total of 0.68 g (45% yield, 98% purity) of Compound 6 was obtained as a white solid. $^1$H NMR (400 MHz, DMSO-$d_6$) δ 11.02 (br s, 1H), 5.17 (s, 1H), 2.45-2.25 (m, 4H), 1.90-1.75 (m, 2H), 1.75-1.65 (m, 4H); $^{13}$C NMR (100 MHz, DMSO-$d_6$) δ 186.22, 103.55, 44.69, 38.35, 31.48, 14.61; MS (m/z) 152.1.

Example 5: Preparation of [1-(2-Oxo-propyl)cyclopropyl]acetic Acid (Compound 15)

To a solution of ethyl acetoacetate (48.8 g) in THF (315.0 mL) was added K$_2$CO$_3$ (51.8 g) under nitrogen, the mixture was heated up to 65° C. A total of 41.23 g of cyclopropylidene acetic acid ethyl ester was added dropwise over 30 min, the reaction mixture was stirred for another 3 h at 65° C. Then, a total of 114.0 g (35% aqueous solution) of NaOH was added dropwise into the mixture over 30 min. The resulting mixture was stirred for an additional 3 h at 65° C. and then cooled to room temperature. Water (250 mL) was added and the organic solvent was removed under reduced pressure. The aqueous solution was adjusted to pH about 3.0 with conc. HCl, and then heated and stirred at 85° C. for 3 h. It was cooled to room temperature and extracted with MTBE (3×150 mL). The combined organic layer was dried over $MgSO_4$. Filtration, followed by concentration, gave 38.5 g (88% by GC purity, yield 79%) of the crude product as yellow oil which was used directly for the next step. $^1$H NMR (400 MHz, $CDCl_3$) δ 10.80 (br s, 1H), 2.51 (s, 2H), 2.30 (s, 2H), 2.08 (s, 3H), 0.55-0.45 (m, 2H), 0.45-0.35 (m, 2H); $^{13}$C NMR (100 MHz, $CDCl_3$) δ 209.0, 178.2, 49.1, 40.5, 30.0, 20.4, 11.1; MS (m/z) 157.2.

Example 6: Preparation of Methyl [1-(2-Oxo-propyl)cyclopropyl]acetate (Compound 16)

To a solution of [1-(2-oxo-propyl)cyclopropyl]acetic acid (38.5 g) in MeOH (460.0 mL) was added 20.0 g of conc. HCL. The mixture was then heated to 65° C. and stirred for 3 h. It was then concentrated to remove methanol. A total of 150 mL of water was added and the aqueous solution was extracted with MTBE (3×150 mL). The combined organic layer was dried over $MgSO_4$. Filtration, followed by concentration, gave 34.1 g (84% by GC purity, yield 81%) of the crude product as colorless oil which was used directly for the next step. $^1$H NMR (400 MHz, $CDCl_3$) δ 3.48 (s, 3H), 2.47 (s, 2H), 2.29 (s, 2H), 2.06 (s, 2H), 0.52-0.46 (m, 2H), 0.44-0.37 (m, 2H); $^{13}$C NMR (100 MHz, $CDCl_3$) δ 208.0, 162.1, 51.2, 49.4, 30.0, 11.5; MS (m/z) 170.8.

Example 7: Preparation of Spiro[2.5]octane-5,7-dione (Compound 3)

To a solution of methyl [1-(2-oxo-propyl)cyclopropyl] acetate (12.0 g) in THF (100 mL) was added 12.1 g of MeONa (30% wt) in MeOH. It was stirred at room temperature overnight. A total of 100 mL of water was added and the solution was concentrated to remove the organic solvent. The resulting aqueous solution was extracted with MTBE (3×50 mL) and then adjusted to pH=2~3 with conc. HCl. It was then extracted with MTBE (3×50 mL). The combined organic layer was dried over $MgSO_4$. Filtration, followed by concentration, gave the crude product as yellow solid. To the crude product was added 12 mL of MTBE, and the slurry was stirred at 5° C. for 30 min. The solid was collected by filtration and washed with cold MTBE (2×6 mL). It was dried under vacuum. A total of 4.8 g (62% yield, 98.6% purity by HPLC) was obtained as light yellow solid. $^1$H NMR (400 MHz, DMSO-$d_6$) δ 11.05 (s, br 1H), 5.25 (s, 1H), 2.15 (s, 4H), 0.35 (s, 4H); $^{13}$C NMR (100 MHz, DMSO-$d_6$) δ 178.61, 103.96, 41.76, 14.95, 10.85; MS (m/z) 138.1.

The invention claimed is:
1. A method of preparing spiro[2.5]octane-5,7-dione having the formula

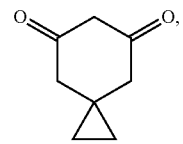

said method comprising:
cyclization of cyclopropylidene carboxylic acid alkyl ester having the formula

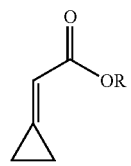

with dialkyl 1,3-acetonedicarboxylate having the formula

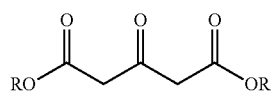

to form 5,7-dioxo-spiro[2.5]octane-4,6-dicarboxylic acid dialkyl ester having the formula

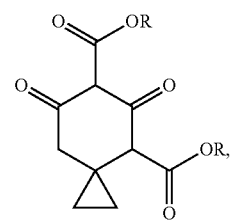

wherein each R may be independently C1-C6 alkyl, and
ester hydrolysis and decarboxylation of 5,7-dioxo-spiro[2.5]octane-4,6-dicarboxylic acid to form spiro[2.5]octane-5,7-dione,
wherein each R may be independently C1-C6 alkyl.

* * * * *